United States Patent [19]

Isaac et al.

[11] 3,959,299
[45] May 25, 1976

[54] HERBICIDAL AMIDE DERIVATIVES

[75] Inventors: Eirlys R. Isaac, Sittingbourne; Peter Kirby, Maidstone, both of England

[73] Assignee: Shell Oil Company, Houston, Tex.

[22] Filed: Aug. 4, 1975

[21] Appl. No.: 601,746

Related U.S. Application Data

[62] Division of Ser. No. 482,935, June 25, 1974, Pat. No. 3,920,675.

[30] Foreign Application Priority Data

July 3, 1973 United Kingdom............... 31604/73

[52] U.S. Cl............................. 260/295 AM; 71/94; 260/295.5 A
[51] Int. Cl.²....................................... C07D 405/12
[58] Field of Search ............. 260/295 AM, 295.5 A; 71/94

[56] References Cited

UNITED STATES PATENTS

| | | | |
|---|---|---|---|
| 3,493,555 | 2/1970 | Wilbert et al. | 260/156 |
| 3,758,485 | 9/1973 | Biniecki et al. | 260/295 AM |
| 3,822,276 | 7/1974 | Meisels et al. | 260/295 AM |

*Primary Examiner*—Norman A. Drezin

[57] ABSTRACT

New compounds of the formula

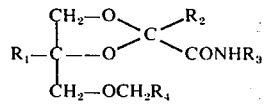

wherein $R_1$ and $R_2$ each is alkyl; $R_3$ is a nitrogen-containing heterocyclic group; and $R_4$ is optionally substituted phenyl, are useful as herbicides.

4 Claims, No Drawings

HERBICIDAL AMIDE DERIVATIVES

This is a division of application Ser. No. 482,935, filed June 25, 1974, now U.S. Pat. No. 3,920,675, issued Nov. 18, 1975.

DESCRIPTION OF THE INVENTION

This invention relates to amide derivatives which are of interest as herbicides.

Accordingly the present invention provides amide derivatives of general formula:

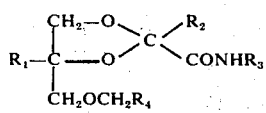

wherein $R_1$ and $R_2$ each represents an alkyl group; $R_3$ represents a nitrogen-containing heterocyclic group; and $R_4$ represents a phenyl group optionally substituted by halogen or by alkyl.

More particularly, the invention is directed to amide derivatives of general formula I wherein $R_1$ and $R_2$ each represents an alkyl group of 1–6 carbon atoms; $R_3$ represents a 5- or 6-membered heterocyclic group containing 1 to 2 nitrogen atoms in the ring and 0 to 1 sulfur atoms in the ring; and $R_4$ represents a phenyl group optionally substituted by fluorine or chlorine or by an alkyl group of 1–6 carbon atoms.

Because of their properties, preferred amide derivatives are those of formula I wherein $R_1$ and $R_2$ each represents an alkyl group of 1–6 carbon atoms, for example methyl, ethyl, or propyl; $R_3$ represents a 5- to 6-membered nitrogen-containing heterocyclic group, for example, thiazolyl, thiadiazolyl or pyridyl; and $R_4$ represents a phenyl group optionally substituted by one or two chlorine atoms or by an alkyl group of 1–6 carbon atoms, for example by methyl.

The compounds of formula I may be prepared by a process which comprises reacting a compound of formula:

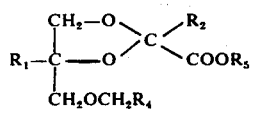

wherein $R_5$ represents an alkyl group, with an amine of the formula:

$$NH_2R_3 \qquad III$$

When $R_5$ is an alkyl group the reaction is suitably carried out in the presence of a strong base, for example an alkali metal hydride such as sodium hydride. The compounds of formula II wherein $R_5$ is alkyl are known compounds, disclosed in Netherlands Patent No. 72,07026.

As mentioned above the amide derivatives of the invention are of interest as herbicides, and the invention includes, therefore, herbicidal compositions comprising a carrier and/or a surface active agent, together with, as active ingredient, an amide derivative of the invention. Likewise the invention also includes a method of combating weeds at a locus which comprises applying to the locus an amide derivative or composition of the invention.

The term "carrier" as used herein means a solid or fluid material, which may be inorganic or organic and of synthetic or natural origin, with which the active compound is mixed or formulated to facilitate its application to the plant, seed, soil or other object to be treated, or its storage, transport or handling.

The surface-active agent may be an emulsifying agent or a dispersing agent or a wetting agent; it may be non-ionic or ionic.

Any of the carrier materials or surface-active agents usually applied in formulating pesticides may be used in the composition of the invention, and suitable examples of these are to be found, for example, in UK Specification No. 1,232,930.

The compositions of the invention may be formulated as wettable powders, dusts, granules, solutions, emulsifiable concentrates, emulsions, suspension concentrates or aerosols. Wettable powders are usually compounded to contain 25, 50 or 75% w of toxicant and usually contain, in addition to solid carrier, 3–10% w of a dispersing agent and, where necessary, 0–10% w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½–10% w of toxicant. Granules are usually prepared to have a size between 10 and 100 BS mesh (1.676–0.152 mm), and may be manufactured by agglomeration or impregnation techniques. Generally, granules will contain ½–25% w active ingredient and 0–10% w of additives such as stabilizers, slow release modifiers and binding agents. Emulsifiable concentrates usually contain, in addition to the solvent and, when necessary, co-solvent, 10–50% w/v active ingredient, 2–20% w/b emulsifiers and 0–20% w/v of appropriate additives such as stabilizers, penetrants and corrosion inhibitors. Suspension concentrates are compounded so as to obtain a stable, non-sedimenting, flowable product and usually contain 10–75% w active ingredient, 0.5–15% w of dispersing agents, 0.1–10% w of suspending agents such as protective colloids and thixotropic agents, 0–10% w of appropriate additives such as defoamers, corrosion inhibitors, stabilizers, penetrants and stickers, and as carrier, water or an organic liquid in which the active ingredient is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick "mayonnaise"-like consistency.

The compositions of the invention may also contain other ingredients, for example, other compounds possessing pesticidal, especially insecticidal, acaricidal, herbicidal or fungicidal properties.

The invention is further illustrated in the following examples. It should be understood, however, that the examples are for the purpose of illustration only and should not be regarded as limiting the invention in any way. In the examples the structure of the compounds was confirmed by elemental analysis and NMR spectral analysis.

EXAMPLE 1

Preparation of 4-Benzyloxymethyl-4-ethyl-2-methyl-1,3-dioxolan-2(N-pyrid-2-yl)carboxamide Ethyl 4-benzyloxymethyl-4-ethyl-2-methyl-1,3-dioxolan-2-carboxylate (8.0g), 2-amino-pyridine (2.45g) and sodium hydride (1.25g of 50% dispersion in oil) were stirred together in dimethyl sulphoxide (50ml) for 16 hours at room temperature. The reaction mixture was poured onto ice and extracted with chloroform. The organic solution was washed twice with water, dried and the solvent evaporated. The residue was purified (chromatography on silica gel using chloroform as eluant) to give desired product 3.1g (33%) as an oil.

Analysis: Calculated for $C_{20}H_{24}N_2O_4$ : C, 67.4; H, 6.8; N, 7.9%. Found : C, 67.4; H, 7.1; N, 7.8%.

EXAMPLES 2–5

Following procedures similar to those given in the previous Example further compounds were prepared, for which physical characteristics are given in the following Table 1.

TABLE I

| Compound | m.p.°C or refractive index |
| --- | --- |
| 2  4-benzyloxymethyl-4-ethyl-2-methyl-1,3-dioxolan-2-(N-thiazol-2-yl)carboxamide | $n_D^{24}$ 1.5210 |
| 3  4-benzyloxymethyl-2,4-dimethyl-1,3-dioxolan-2-(N-pyrid-4-yl)carboxamide | $n_D^{24}$ 1.5105 |
| 4  4-benzyloxymethyl-4-ethyl-2-methyl-1,3-dioxolan-2-(N-5-methyl-thiadiazol-2-yl)carboxamide isomer A | |
| 5  4-benzyloxymethyl-4-ethyl-2-methyl-1,3-dioxolan-2-(N-5-methyl-thiadiazol-2-yl)carboxamide | m.p. 137–140 | a compound of the invention, and in the foliar spray tests the seedling plants were sprayed with such a formulation.

The soil used in the tests was a steam-sterilized, modified John Innes Compost mixture in which half the peat, by loose bulk, had been replaced by vermiculite.

The formulations used in the tests were prepared by diluting with water solutions of the compounds in acetone containing 0.4% by weight of an alkylphenol/ethylene oxide condensate available under the trade name Triton X-155. In the soil spray and foliar spray tests the acetone solutions were diluted with an equal volume of water and the resulting formulations applied at two dosage levels corresponding to 10 and 1 kilograms of active material per hectare respectively in a volume equivalent to 400 liters per hectare. In the soil drench tests one volume of the acetone solution was diluted to 155 volumes with water and the resulting formulation applied at one dosage level equivalent to 10 kilograms of active material per hectare in a volume equivalent to approximately 3,000 liters per hectare.

The herbicidal effects of the compounds were assessed visually seven days after spraying the foliage and drenching the soil and eleven days after spraying the soil, and were recorded on a 0–9 scale. A rating 0 indicates no effect on the treated plants, a rating 2 indicates a reduction in fresh weight of stem and leaf of the plants of approximately 25%, a rating 5 indicates a reduction of approximately 55%, a rating 9 indicates a reduction of 95% etc.

EXAMPLE 6

HERBICIDAL ACTIVITY

To evaluate their herbicidal activity, compounds of the invention were tested using as a representative range of plants:- maize, *Zea mays* (Mz); rice, *oryza sativa* (R); barnyard grass, *Echinchloa crusgalli* (BG); pea, *Pisum sativum* (P); linseed, *Linum usitatissium* (L); mustard, *Sinapis alba* (M); and sugar beet, *Beta vulgaris* (SB).

The tests fall into two categories, pre-emergence and post-emergence. The pre-emergence tests involved spraying a liquid formulation of the compound onto the soil in which the seeds of the plant species mentioned above had recently been sown. The post-emergence tests involved two types of test, viz. soil drench and foliar spray tests. In the soil drench tests the soil in which seedling plants of the above species were growing, was drenched with a liquid formulation containing The results of the tests are set out in Table 2.

TABLE 2

| Example | Dosage kg/ha | Post-Emergence Soil Drench | | | | | | | Post-Emergence Foliar Spray | | | | | | | Pre-emergence Soil Spray | | | | | | |
| --- | --- | --- | --- | --- | --- | --- | --- | --- | --- | --- | --- | --- | --- | --- | --- | --- | --- | --- | --- | --- | --- | --- |
| | | Mz | R | BG | P | L | M | SB | Mz | R | BG | P | L | M | SB | Mz | R | BG | P | L | M | SB |
| 1 | 10 | 7 | 6 | 8 | 5 | 8 | 3 | 5 | 7 | 4 | 8 | 5 | 7 | 5 | 5 | 9 | 9 | 9 | 9 | 7 | 7 | 7 |
| | 1 | | | | | | | | 2 | 0 | 7 | 5 | 6 | 0 | 5 | 8 | 9 | 9 | 9 | 7 | 3 | 3 |
| 2 | 10 | 7 | 5 | 7 | 4 | 7 | 3 | 6 | 7 | 4 | 8 | 5 | 7 | 2 | 5 | 9 | 9 | 9 | 9 | 7 | 6 | 7 |
| | 1 | | | | | | | | 0 | 0 | 7 | 4 | 7 | 0 | 5 | 8 | 9 | 9 | 8 | 7 | 5 | 3 |
| 3 | 10 | 7 | 3 | 7 | 0 | 0 | 0 | 3 | 3 | 4 | 8 | 7 | 8 | 8 | 4 | 9 | 9 | 9 | 8 | 7 | 7 | 5 |
| | 1 | | | | | | | | 0 | 0 | 1 | 2 | 1 | 2 | 2 | 0 | 6 | 8 | 0 | 0 | 0 | 0 |

We claim as our invention:

1. An amide derivative of the formula

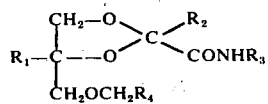

wherein $R_1$ and $R_2$ each represents an alkyl group of 1 to 6 carbon atoms; $R_3$ represents pyridyl; and $R_4$ represents a phenyl group optionally substituted by one or two chlorine atoms or by an alkyl group of 1 to 6 carbon atoms.

2. An amide derivative according to claim 1 wherein $R_3$ represents 2-pyridyl.

3. An amide derivative according to claim 2 wherein $R_1$ represents methyl or ethyl; $R_2$ represents methyl and $R_4$ represents phenyl.

4. A method of combating weeds at a locus which comprises applying to that locus a herbicidally effective amount of an amide derivative as claimed in claim 1.

* * * * *